US00PP24549P3

(12) United States Plant Patent
Olesen

(10) Patent No.: US PP24,549 P3
(45) Date of Patent: Jun. 17, 2014

(54) MINIATURE ROSE PLANT NAMED 'POULPAR071'

(50) Latin Name: ***Rosa* hybrid**
Varietal Denomination: Poulpar071

(75) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 13/507,031

(22) Filed: May 31, 2012

(65) Prior Publication Data

US 2013/0326746 P1 Dec. 5, 2013

(51) Int. Cl.
*A01H 5/00* (2006.01)

(52) U.S. Cl.
USPC ..... Plt./116

(58) Field of Classification Search
USPC ..... Plt./116, 119, 120, 121
See application file for complete search history.

*Primary Examiner* — Kent L Bell

(57) ABSTRACT

A new miniature rose plant that has abundant, orange and pink blend flowers and attractive foliage. The variety successfully propagates from softwood cuttings and is suitable for year-round production in commercial glasshouses. This new and distinct variety has shown to be uniform and stable in the resulting generations from asexual propagation.

1 Drawing Sheet

Botanical designation: *Rosa* hybrid.
Variety denomination: 'Poulpar071'.

SUMMARY OF THE INVENTION

The present invention constitutes a new and distinct variety of miniature rose plant which originated from a controlled crossing between the female seed parent, an unnamed seedling, and the male pollen parent, also an unnamed seedling.

The two parents were crossed during the summer of 2006 and the resulting seeds were planted in a controlled environment in Fredensborg, Denmark. The new variety, named 'Poulpar071', originated as a single seedling from the stated cross.

The new variety may be distinguished from its male pollen parent and female seed parent primarily by flower coloration and growth habit.

The objective of the hybridization of this rose variety was to create a new and distinct variety for use in the floral industry with unique qualities, such as:

1. Uniform and abundant pink and orange blend flowers;
2. Vigorous, but compact growth when propagated on its own roots;
3. Durable flowers and foliage which make a variety suitable for distribution in the floral industry; and
4. Year-round flowering under glasshouse conditions.

This combination of qualities is not present in previously available commercial cultivars of this type, known to the inventor, and distinguish 'Poulpar071' from all other varieties of which we are aware.

As part of the rose development program, Mogens N. Olesen germinated the seeds from the aforementioned hybridization during winter of 2006 and conducted evaluations on the resulting seedlings in a controlled environment in Fredensborg, Denmark. 'Poulpar071' was selected in the spring of 2007 by the inventor as a single plant from the progeny of the aforementioned hybridization.

Asexual reproduction of 'Poulpar071' by traditional budding and rooted cuttings was first done by Mogens N. Olesen in the nursery in Fredensborg, Denmark in July, 2007. This initial and other subsequent asexual propagations conducted in controlled environments have demonstrated that the characteristics of 'Poulpar071' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulpar071'.

Specifically illustrated in the drawing are flowers at various stages of development, flower in parts, leaves, and stems.

DETAILED DESCRIPTION OF THE VARIETY

The following is a description of 'Poulpar071', as observed in its growth in a glasshouse in Half Moon Bay, Calif. Observed plants are 3 months of age, and were grown on their own roots in 4 inch pots. Color references are made using The Royal Horticultural Society (London, England) Colour Chart, 2001, except where common terms of color are used.

For a comparison, several physical characteristics of the rose variety 'Poulpar041', U.S. Plant Pat. No. 17,889 are compared to 'Poulpar071' in Chart 1.

CHART 1

| | 'Poulpar071' | 'Poulpar041' |
|---|---|---|
| Petal Count | 70 | 35 |
| Flower Diameter | 50 to 60 mm | 35 to 40 mm |
| Genaral Tonality of Flower Color | Orange Red Group 32B | Red Group 38A to Red Group 41C with intonations of Yellow Group 11A to 11B and Yellow Orange Group 22D |

Flower and Flower Bud

Blooming habit: Continuous.

Flower bud:

*Size.*—Upon opening, 25 mm in length from base of receptacle to end of bud. Bud diameter is 13 mm.

*Bud form.*—Urceolate.

*Bud color.*—As sepals divide petals are Orange Red N34C and Red 38A to 38B.

*Sepal inner surface.*—Color: Yellow-Green Group 144B. Surface: Smooth.

*Sepal outer surface.*—Color: Yellow-Green Group 144B. Texture: Smooth.

*Sepal shape.*—Apex: Cirrhose. Base: Flat at union with receptacle.

*Sepal margin.*—Margins have very weak foliaceous appendages on three of the five sepals.

*Sepal size.*—25 mm long by 10 mm wide.

*Receptacle.*—Texture: Smooth. Shape: Urn shaped. Size: 5 mm tall by 8 mm wide. Color: Yellow-Green Group 144B.

*Pedicel.*—Surface: Smooth. Length: 25 to 35 mm. Diameter: 3 mm on average. Color: Yellow-Green Group 144A. Strength: Strong.

Flower bud development: Flower buds are borne singly.

Flower bloom:

*Fragrance.*—None, to light floral.

*Duration.*—The blooms have a duration on the plant of approximately 25 days. Petals adhere to receptacle after flowers have matured.

*Size.*—Flower diameter is 50 to 60 mm when open. Flower depth is 25 mm.

*Flower shape.*—General shape is a hybrid tea, which opens fully to become a quartered rosette.

*Shape of flower, side view.*—Upon opening the upper portion is flat. The lower portion is a flattened convex.

Petalage: Under normal conditions, flowers have 70 petals total, 15 of which are petaloids.

Petal color:

*Upon opening, outer petals.*—Upper surface: Orange Group 29A. Lower surface: Orange Group 29B with shaded intonations of Red Group 52B at the middle zone.

*Upon opening, inner petals.*—Upper surface: Orange Group 29A with very lightly shaded intonations of Red Group 38A. Lower surface: Orange Group 29A.

*Basal petal spots, upon opening.*—Upper surface: Yellow Group 12D. Lower surface: Yellow Group 12D.

*After opening, outer petals.*—The lower and upper surfaces are Orange Group 29A with intonations of Orange Red Group N34C at the middle zone.

*After opening, inner petals.*—Upper surface: Orange Group 29A with light intonations of Red Group 38A. Lower surface: Orange Group 29A.

General tonality: Open flowers are Orange Red Group 32B. Tonality changes to Orange Group 29A and Red Group 38A as the flower ages.

Petals:

*Petal reflex.*—Strong.

*Margin.*—Entire, with a slight point at the center, with moderate undulations.

*Shape.*—Generally broad and elliptic. Apex shape: Rounded. Base shape: Acute.

*Size.*—25 mm (l)×32 mm (w).

*Texture.*—Smooth.

*Thickness.*—Average.

Petaloids:

*Quantity.*—15 on average.

*Shape.*—Irregular, and asymmetric. The apex and base are acute.

*Color.*—Orange Group 29A with light intonations of Red Group 38A.

*Size.*—15 mm (l)×6 mm (w).

Reproductive organs:

*Pollen.*—None observed.

*Anthers.*—Size: 2 mm in length. Color: Yellow Group 8C. Quantity: 38 on average.

*Filaments.*—Color: Yellow Group 8D. Length: 3 mm.

*Pistils.*—Length: 3 mm. Quantity: 40 on average.

*Stigmas.*—Color: Yellow Group 8C.

*Styles.*—Color: Yellow Group 8C.

*Location of stigmas.*—Level, relative to the length of the filaments and the height of the anthers.

*Hips.*—None Observed.

Plant

Plant growth: Upright. Plants are 15 to 20 cm in height, and 15 cm wide.

Stems:

*Color.*—Juvenile growth: Yellow-Green Group 144A. Mature growth: Green Group 138A.

*Length.*—Canes are 12 to 15 cm from the base of the plant to the flowering portion.

*Diameter.*—3 to 4 mm.

*Internodes.*—On mature canes, there is an average distance of 16 mm between nodes.

*Surface texture.*—Young wood: Smooth. Older wood: Smooth.

Long prickles: None observed.

Plant foliage:

*Compound leaf.*—80 mm (l)×50 mm (w).

*Quantity.*—7 leaves per 10 cm of stem on average.

*Color of juvenile foliage.*—Upper side: Yellow-Green Group 146A. Lower side: Yellow-Green Group 146A.

*Color of mature foliage.*—Upper side: Yellow-Green Group 147A. Lower side: Yellow-Green Group 147B.

Plant leaves and leaflets:

*Stipules.*—Size: About 3 mm in length. Quantity: 2 per compound leaf. Shape: Linear, slightly broad based with outward extending apices. Margins: Finely serrated with sparse stipitate glands. Color: Yellow-Green Group 144A.

*Petiole.*—Length: 15 mm on average. Diameter: About 2 mm. Upper surface: Yellow-Green Group 144A. Lower surface: Yellow-Green Group 144B.

*Rachis.*—Length: About 25 mm. Upper surface: Yellow-Green Group 144A. Lower surface: Yellow-Green Group 144B.

*Leaflet.*—Quantity: Normal number of leaflets on leaves in the middle of the stem is 5 leaflets. Margins: Serrated. Size: Average size of the terminal leaflet on normal leaves is 40 mm in length by 20 mm wide. Shape: Generally elliptical. Base: Rounded. Apex: Cuspidate. Texture: Smooth. Thickness: Average. Arrangement: Odd pinnate. Venation: Reticulate. Glossiness: Moderately glossy.

Disease resistance: Above average resistance to powdery and downy mildew, rust, black spot, and *Botrytis* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

The invention claimed is:

1. A new and distinct variety of rose plant of the miniature class named 'Poulpar071', substantially as illustrated and described herein, due to its abundant, orange and pink blend flowers, vigorous growth, compact habit, suitability for production from softwood cuttings in pots, and durable flowers and foliage that make the variety suitable for distribution in the floral industry.

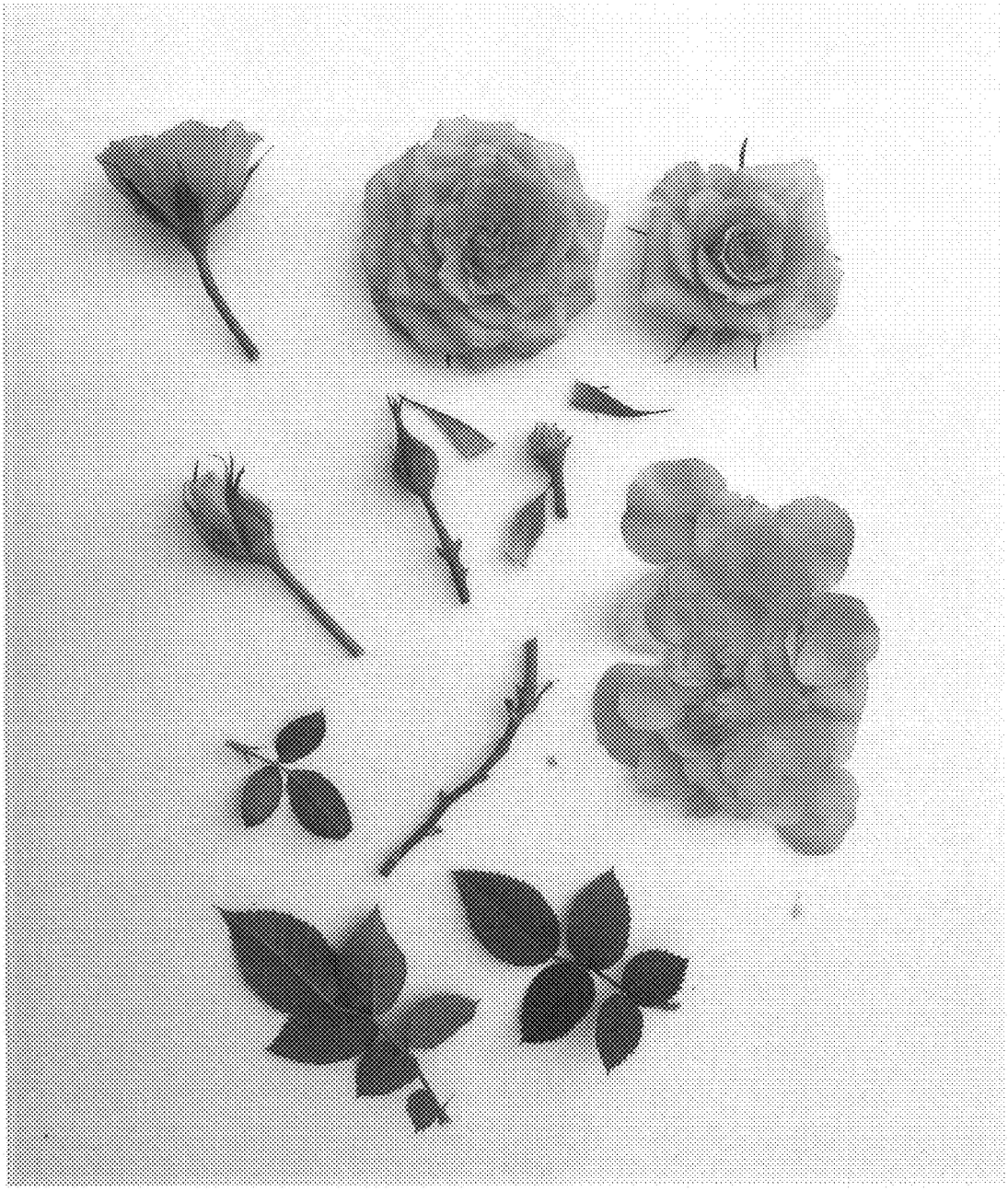

* * * * *